US007843565B2

(12) United States Patent
Wu et al.

(10) Patent No.: US 7,843,565 B2
(45) Date of Patent: Nov. 30, 2010

(54) OPTICAL GAS MONITOR

(75) Inventors: Sheng Wu, San Gabriel, CA (US); Andrei Deev, Pasadena, CA (US); Steve L. Palm, Escondido, CA (US); Yongchun Tang, Walnut, CA (US); William A. Goddard, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 548 days.

(21) Appl. No.: 11/807,538

(22) Filed: May 29, 2007

(65) Prior Publication Data

US 2007/0291271 A1 Dec. 20, 2007

Related U.S. Application Data

(60) Provisional application No. 60/809,000, filed on May 26, 2006.

(51) Int. Cl.
*G01N 21/25* (2006.01)
(52) U.S. Cl. ....................................................... 356/416
(58) Field of Classification Search ................. 356/416, 356/437
See application file for complete search history.

(56) References Cited

U.S. PATENT DOCUMENTS 5,191,386 A * 3/1993 Grebe ........................ 356/28.5

5,637,872 A 6/1997 Tulip

OTHER PUBLICATIONS

Avetisov, V. G., et al., "Two-Ton Frequency-Modulation Spectroscopy for Quantitative Measurements of Gaseous Species: Theoretical, Numerical, and Experimeental investigation of Line Shapes", *Applied Optics*, (Aug. 20, 1996),4705-4723.
Cooper, David E., et al., "Two-Tone Optical Heterodyne Spectroscopy With Diode Lasers: Theory of Line Shapes and Experimental Results", *J. Optical Socienty of America B*, vol. 4, No. 4, (Apr. 1987),470-480.
Cuccoli, Fabrizio , et al., "Infrared Tomographic System for Monitoring the Two-Dimensional Distribution of Atmospheric Pollution Over Limited Areas", *IEEE Transactions Geoscience and Remote Sensing*, vol. 38, No. 2, (Jan. 2000),155-168.
Gehrtz, Manfred , et al., "Quantum-limited Laser Frequency-Modulation Spectroscopy", *J. Optical Society of America*, vol. 2, No. 9, (Sep. 1985),1510-1526.
Modugno, G. , et al., "Fundamental Noise Sources in a High-Sensitivity Two-Ton Frequency Modulation Spectrometer and Detection of CO2 at 1.6um and 2um", *Applied Physics B*, (1998),289-296.

* cited by examiner

*Primary Examiner*—Tarifur Chowdhury
*Assistant Examiner*—Abdullahi Nur

(57) ABSTRACT

A frequency modulated spectroscopy system, including a photo-detector, a band-pass filter to filter the output of the photo-detector, and a rectifier to demodulate. The band-pass filter has a relatively high Q factor. With the high Q factor band-pass filter and rectifier, a reference sinusoid is not required for demodulation, resulting in phase-insensitive spectroscopy. Other embodiments are described and claimed.

11 Claims, 4 Drawing Sheets

OPTICAL GAS MONITOR

BENEFIT OF PROVISIONAL APPLICATION

This patent application claims the benefit of Provisional Application No. 60/809,000 filed 26 May 2006.

GOVERNMENT INTEREST

The U.S. Government has certain rights in this invention pursuant to Grant No. DE-FC26-04NT42212/T-103181 awarded by the Department of Energy.

FIELD

The present invention relates to spectroscopy, and more particularly, to frequency modulation spectroscopy.

BACKGROUND

Laser frequency modulation (FM) spectroscopy is a commonly used method for optical detection of trace gases in the atmosphere. FIG. 1 illustrates, at the system level, a FM spectroscopy system and its accompanying signal processing system. Source 102 provides the laser radiation that is frequency modulated. Source 102 may be a tunable diode laser, or a combination of a laser and an electro-optical modulator. The frequency of the laser radiation is usually modulated by either modulating the injection current of the diode laser or by modulating its phase. The phase may be modulated by using a non-linear crystal to perform electro-optical modulation.

A major contribution to source noise comes from 1/f noise. The power density of this type of noise is inversely proportional to the frequency. FM spectroscopy reduces the contribution of 1/f noise by performing detection at radio frequencies where its power is significantly lower. Accordingly, the frequency modulation is usually within the RF (radio frequency) band. The laser light is transmitted through the region to be monitored (measured).

In ideal single-tone FM modulation, spectral power is present at the carrier optical frequency of the laser radiation, and at harmonics of the frequency modulation, where the power spectral power is symmetrical about the carrier frequency. Let $\omega_C$ denote the carrier frequency of a laser source, n an index denoting a harmonic, and $\omega_{RF}$ denote the modulation frequency. For ideal FM spectroscopy, because the spectral power is symmetrical about the optical carrier frequency, the radiated spectral power at frequency $\omega_C+n\omega_{RF}$ is the same as the power at frequency $\omega_C-n\omega_{RF}$. Gases to be detected have an absorption gradient with respect to frequency. If the carrier frequency and at least one pair of harmonics are in a frequency range for which there is an absorption gradient, then the radiated laser is modulated by the gas so that its spectral power is no longer symmetrical about its carrier frequency. For example, if the carrier frequency and the first harmonic are such that $\omega_C+\omega_{RF}$ and $\omega_C-\omega_{RF}$ under go different absorption rates, then the spectral power at $\omega_C+\omega_{RF}$ will no longer be equal to the spectral power at $\omega_C-\omega_{RF}$. The result is that the intensity of the radiation now has a sinusoidal component at frequency $\omega_{RF}$, and that the amplitude of this frequency component is indicative of the absorption. That is, the imbalance in the frequency domain due to the absorption gradient now imparts an amplitude modulated RF component onto the intensity of the laser radiation.

In the particular system of FIG. 1, RF oscillator 104 provides the frequency source for the FM modulation. Detector 106 receives the radiation, and outputs an electrical signal indicative of the received radiation. Because the amplitude modulated component is in the RF band, the front end of the signal processing system is operated in the RF band. The signal output of detector 106 is high-pass filtered by filter 108. The signal processing system in FIG. 1 performs homodyne detection, a common technique in FM spectroscopy. The detector signal is mixed with a reference sinusoidal signal at the desired harmonic of the modulation frequency. The reference sinusoidal signal is generated from the output of RF oscillator 104. The phase of the reference sinusoidal signal is controlled by phase shift circuit 110. Note that the output signal of RF oscillator 104 may be multiplied by a factor so to detect at a desired harmonic. In the particular example of FIG. 1, the output of RF oscillator 104 is up-converted by a factor of 2. The reference sinusoidal signal (the output of phase shifter 110) is mixed with the output of high-pass filter 108 by mixer 112, and the output of mixer 112 is low-pass filtered by filter 114 to provide a signal indicative of the amplitude modulation. Data acquisition 116 performs analog-to-digital conversion of the output of filter 114, and applies other digital signal processing functions and data acquisition tasks.

In some applications, laser source 102 is frequency modulated at two closely spaced RF frequencies. The resulting spectral power is at the carrier frequency, and at sums and differences of multiples of the two RF frequencies. This is commonly referred to as two-tone frequency modulation. The two-tone FM technique is well suited for spectroscopy of atmospherically broadened lines. In this technique, the RF frequencies are chosen close to, or greater than, the width of the absorption feature. Detection is performed at the difference frequency between the two tones, which is typically in the low MHz range. This permits the use of low-bandwidth detectors and signal amplifiers.

Homodyne detection is a phase-sensitive detection technique because the amplitude of the output signal from low-pass filter 114 is dependent on the phase difference between the reference sinusoid signal from phase shifter 110 and the phase of the RF signal provided by detector 106 and filter 108. This phase difference is usually adjusted to maximize the output signal by phase shifting the reference sinusoidal signal. During a measurement, the relative phase should be fixed because fluctuations in the phase will lead to fluctuations in the output signal of filter 114. However, maintaining the phase in an open-air long-path application may be difficult due to phase noise. Fluctuations of the refractive index in the atmosphere due to convection lead to variations of the phase of the detected signal, and therefore, noise in the spectrum.

DESCRIPTION OF EMBODIMENTS

In the description that follows, the scope of the term "some embodiments" is not to be so limited as to mean more than one embodiment, but rather, the scope may include one embodiment, more than one embodiment, or perhaps all embodiments.

Embodiments of the present invention utilize one, or more, band-pass filters having a relatively high Q factor. As is well known, the Q factor of an oscillating system may be defined as $$Q \equiv \omega_0 \frac{\text{Energy Stored}}{\text{Power Loss}},$$

where $\omega_0$ is the natural oscillation frequency (in radians) of the oscillating system. The bandwidth of a damped oscillator, denoted as $\Delta\omega$, is related to the Q factor by $$\Delta\omega = \frac{\omega_0}{Q}.$$

The response of a high Q factor system is large for an input signal having a frequency of oscillation close or equal to $\omega_0$, and the response falls off very rapidly when the frequency of an input signal varies from $\omega_0$. For band-pass filters, in the language of electronics, $\omega_0$ is the center frequency of the band-pass filter, and $\Delta\omega$ is the bandwidth.

Figure 3:
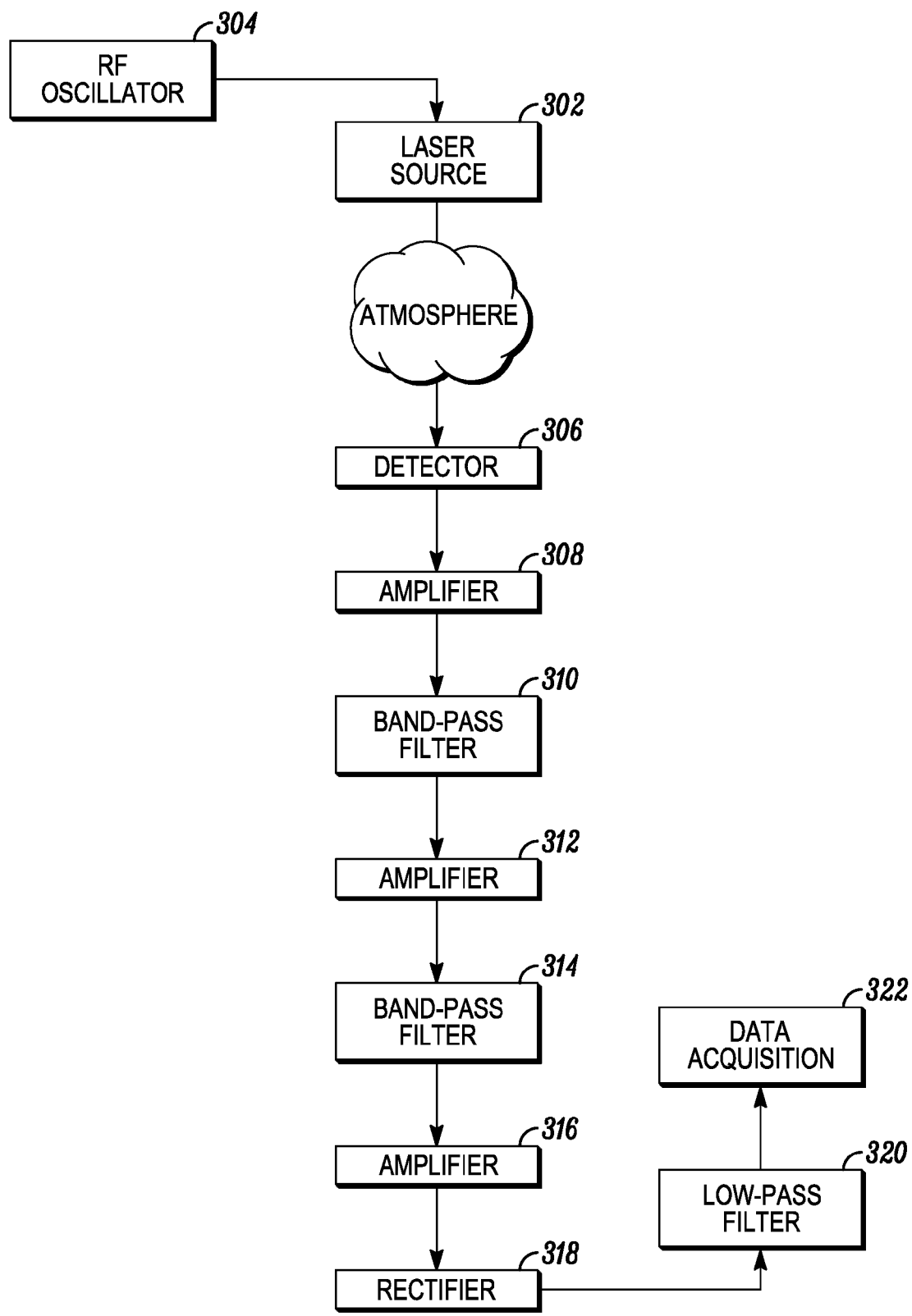
FIG. 3 illustrates a frequency modulation spectroscopy system and a signal processing system according to an embodiment of the present invention.

An example of a laser and signal processing system according to an embodiment of the present invention is illustrated in FIG. 3. Laser source 302 is frequency modulated by RF oscillator 304. Detector 306 provides a signal indicative of the received laser radiation, which is amplified by amplifier 308. Filter 310 is a band-pass filter having a relatively high Q factor. Some embodiments may utilize a crystal filter for filter 310. Crystal filters are readily available with Q factors in the range of 1000 to 2000, and even higher, and at specific center frequencies. For example, crystal filters with center frequencies 10.7 MHz, 21.4 MHz, 45 MHz, 55 MHz, 70 MHz, and 90 MHz are readily available, with various bandwidths, depending upon the center frequency, and with transfer functions with various numbers of poles.

Crystal filters are commonly used in electronic components and utilize resonances in quartz crystals. Although a crystal filter can offer a relatively high Q factor, both the center frequency and bandwidth are fixed for a particular crystal. Accordingly, embodiments of the present invention frequency modulate the laser source so that a desired harmonic matches the center frequency of the crystal filter. For example, if the laser source is frequency modulated at a single RF frequency (single-tone frequency modulation spectroscopy), then the RF frequency is chosen such that a desired harmonic of the RF frequency matches the center frequency of the crystal filter. The laser source may be tuned across an absorption line of the species of interest by slowly ramping the laser injection current.

For the case of frequency modulating the laser source at two closely spaced RF frequencies (two-tone frequency modulation spectroscopy), the RF frequencies may be chosen such that a harmonic of the difference in the two frequencies matches the center frequency of the crystal filter, where the center of the two RF frequencies is chosen to maximize the absorption difference of a spectral feature. Note that a harmonic of the difference in the two frequencies, as referred to above, means $n\omega_1+m\omega_2$, where $\omega_1$ and $\omega_2$ are the frequencies of the two tones, and n and m are integers (positive or negative).

Several stages of filtering and amplification may be used to achieve a higher signal-to-noise ratio. For example, in the particular embodiment of FIG. 3, amplifier 312 amplifies the output of filter 310, which is then band-pass filtered by filter 314. Amplifier 316 provides further amplification. Rectifier 318 rectifies the output of amplifier 316, and filter 320 provides low-pass filtering. The combination of rectifier 318 and low-pass filter 320 performs envelope detection, so that amplitude demodulation is performed by the signal processing system of FIG. 3. The resulting amplitude is provided to data acquisition module 322. Some embodiments may employ only one stage of amplification and band-pass filtering, so that the output of band-pass filter 310 is provided to rectifier 318.

By using one or more band-pass filters having a relatively high Q factor, note that the embodiment of FIG. 3 does not require a reference sinusoid to perform Homodyne detection. That is, a reference sinusoid is not mixed with a received signal. The DC signal provided by rectifier 318 and low-pass filter 320 is dependent on only the detected signal amplitude but not on its phase, and therefore the embodiment of FIG. 3 is expected to be relatively insensitive to the phase noise introduced by atmospheric fluctuations and changes in the optical path length.

For some embodiments, in order to achieve higher optical power, the radiation of the un-modulated laser source (e.g., a diode laser) may be amplified by an amplifier, such as an Erbium-Doped Fiber Amplifier (EDFA), and the amplified radiation may be modulated by a separate modulator with two modulation frequencies for two-tone FM.

Data acquisition module 322 performs one or more signal processing functions. One such function is to mitigate fluctuations in the demodulated output that are not due to the absorption gradient of the species to be detected. That is, even if there are no species with absorption gradients, in practice there is nevertheless an amplitude modulated sinusoidal component in the intensity of the laser radiation. For example, residual amplitude modulation (RAM) of the laser power at the demodulation frequency is usually present due to non-linearity in the laser response to the external modulation or to non-ideal performance of the modulation source. Data acquisition module 322 may be used to cancel this laser power fluctuation by dividing the demodulated signal by the DC voltage from the photo-detector, which is proportional to the received laser power. Some or all of the functions performed by data acquisition module 322 may be realized in special purpose hardware, firmware, or software running on one or more programmable processors.

Figure 4:
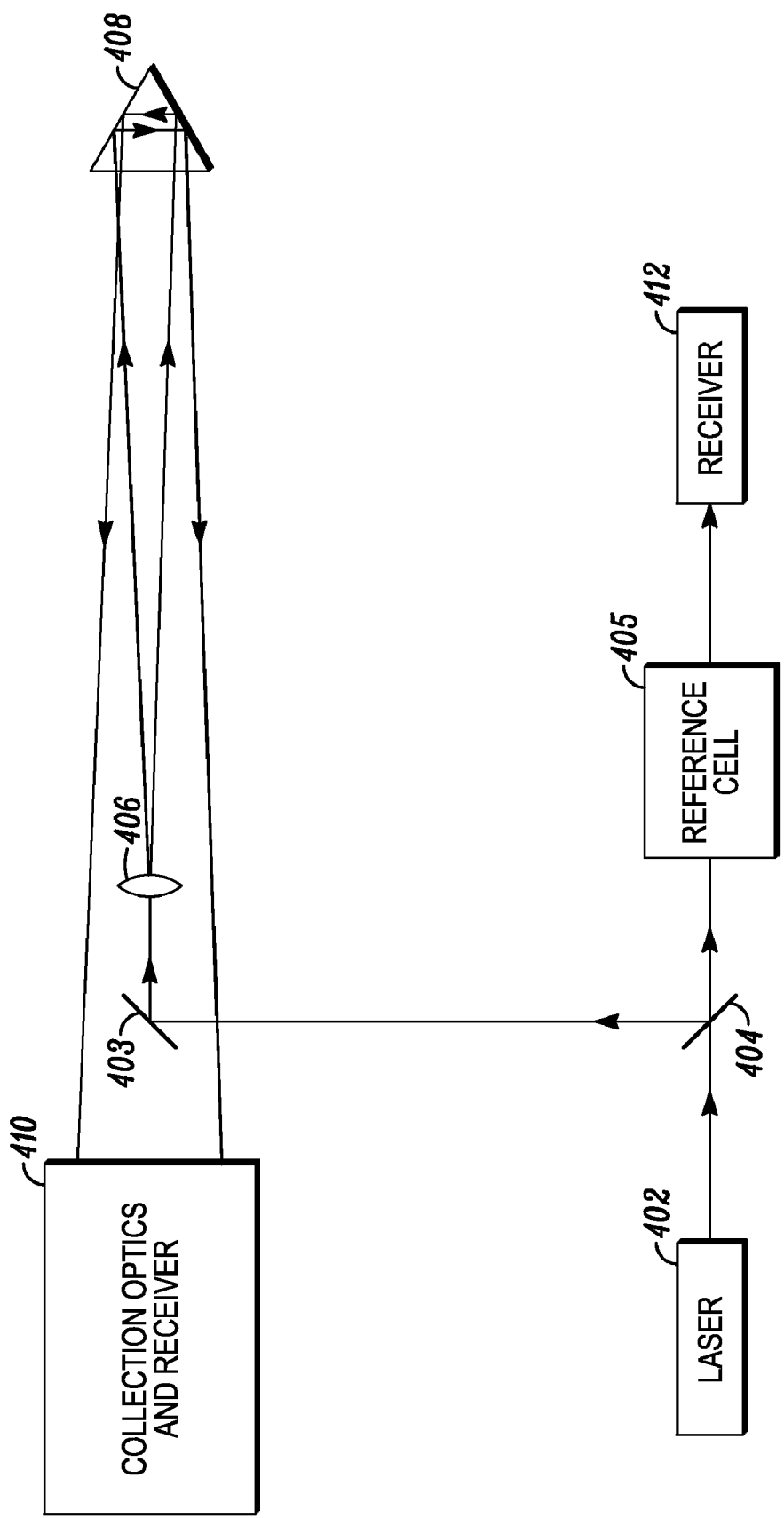
FIG. 4 illustrates a frequency modulation spectroscopy system with reference cell according to an embodiment of the present invention.

FIG. 4 illustrates (not to scale) a spectroscopy system with a reference cell according to an embodiment of the present invention. The radiation from laser source 402 is split by fiber splitter 404 into two beams, one to be launched into the atmosphere to be measured, and another to be launched into reference cell 405. Reference cell 405 includes the species of interest at known concentrations. Mirror 403 reflects one of the beams into optics 406. Optics 406 spreads the radiation beam that is launched into the atmosphere (the open path) to be monitored, and this radiation is reflected by retro-reflector 408 back to collection optics and receiver 410. The beam may be amplified by an Erbium-doped Fiber Amplifier (EDFA) prior to collimation. The receiver component of collection optics and receiver 410 is the embodiment illustrated in FIG. 3, or variations of the embodiment of FIG. 3 in which there may be a different number of stages comprising a band-pass filter and amplifier. Receiver 412 is also similar to that of collection optics and receiver 410, except that the included optical system may be different.

The system of components for launching the open-path radiation beam may be mounted on an optical mount to allow adjustment of the beam direction. That is, the components in FIG. 4, excluding retro-reflector 408, may also include an optical mount, and more than one retro-reflector may be positioned at different directions. As the components on the optical mount are rotated toward the various retro-reflectors, different regions of the atmosphere may be probed.

A retro-reflector may include single or multiple corner cube reflectors, and may be placed in a remote location in the monitoring area within line of sight to the launcher and collection optics. The collection optics may include several mirrors or lenses, e.g., a telescope. The radiation-passing through reference cell 405 is also focused onto a photo-detector, where receiver 412 performs the signal processing indicated by FIG. 3.

Figure 1:
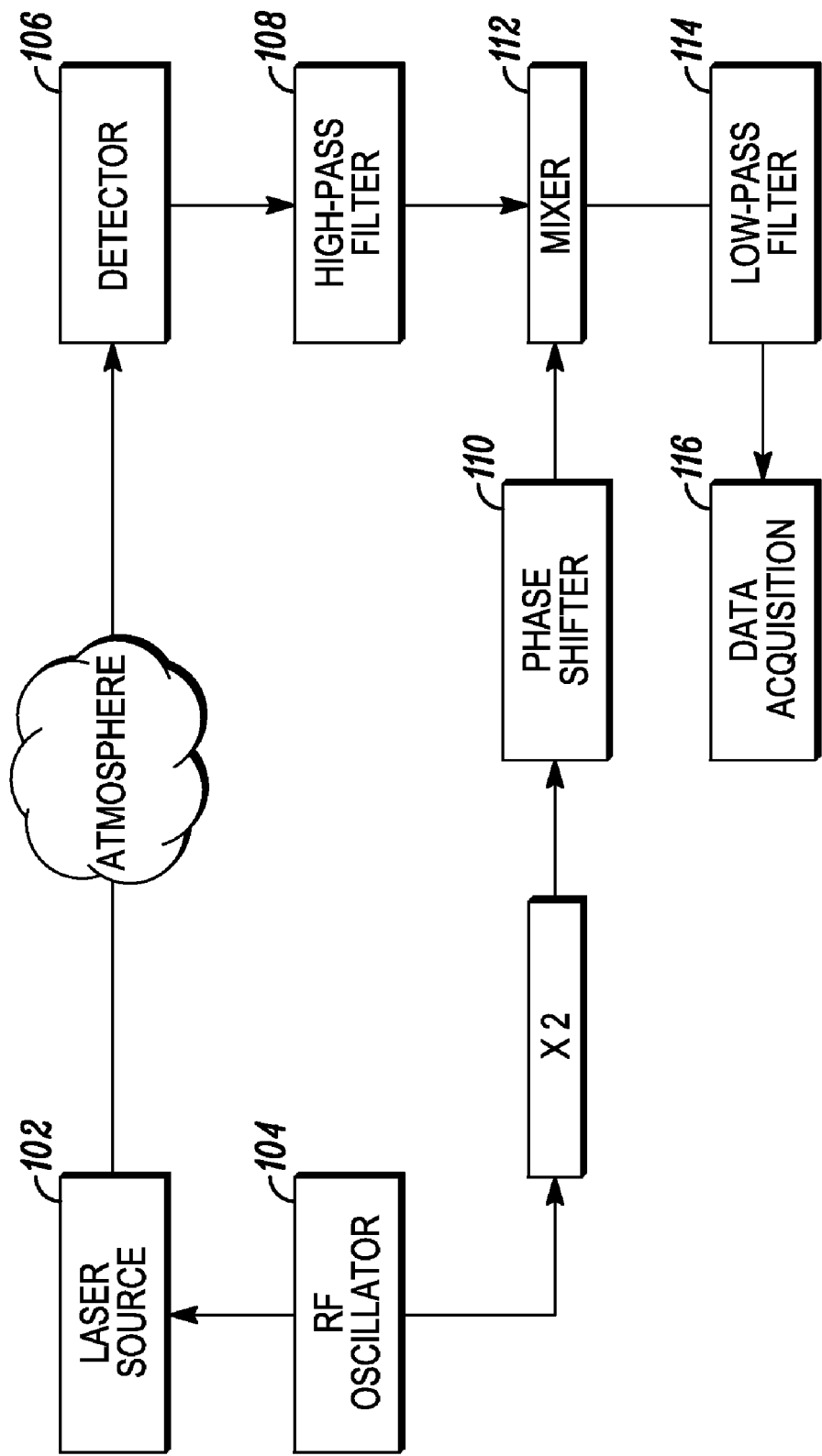
FIG. 1 illustrates a prior art frequency modulation spectroscopy system with homodyne signal processing.
Figure 2:
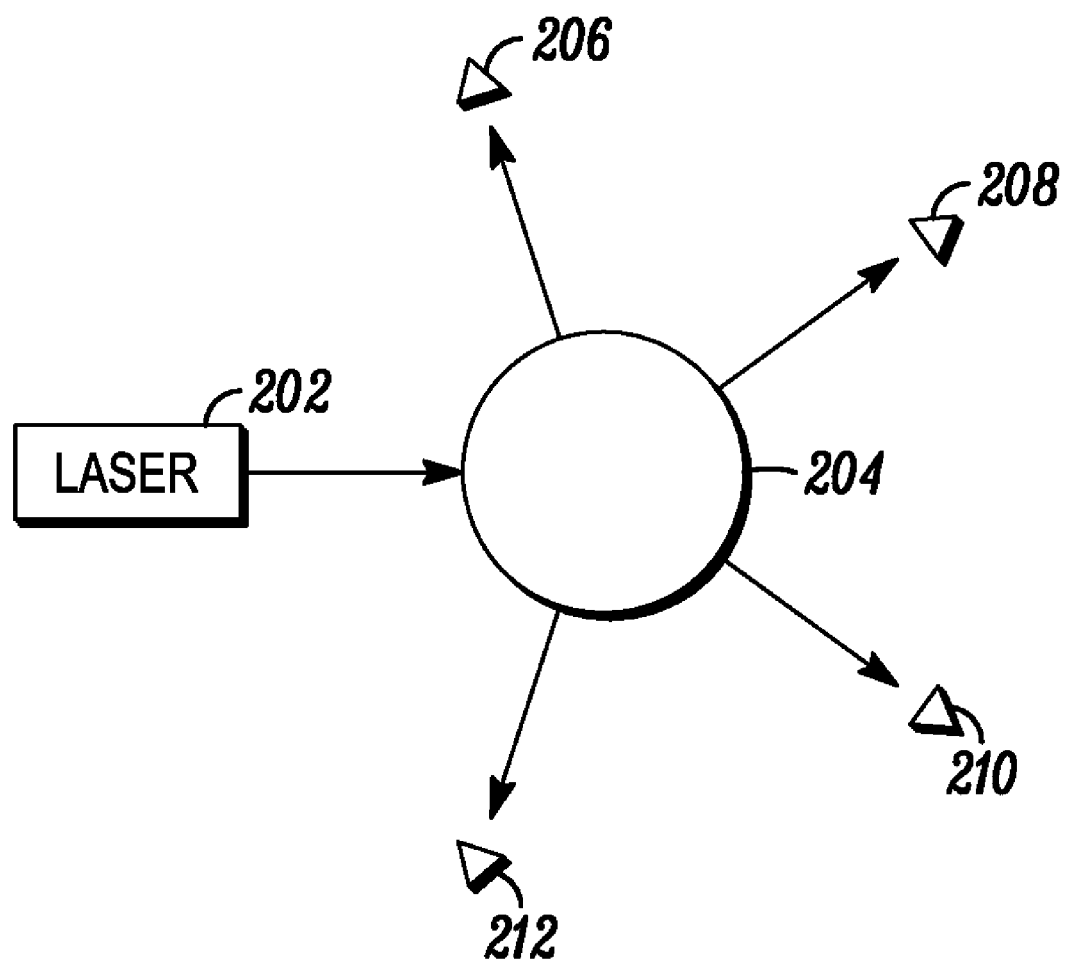
FIG. 2 illustrates a frequency modulation spectroscopy system according to an embodiment of the present invention.

For some embodiments, additional splitters or switches may be employed to provide additional laser beams to probe other regions of the atmosphere at the same time, or at different times using a time-division multiplexing approach. This is illustrated in FIG. 2, showing a beam from laser 202 split into several beams by component 204. Component 204 may also be a switch or system of switches, whereby a single beam is directed to one of retro-reflectors 206, 208, 210, or 212. For simplicity, not shown are the reflected beams, collection optics, and detector. In the time-division multiplexing approach, a single detector may be used, where its position may be oriented to receive the reflected beam, or collection optics and one or more mirrors may be used to refract and reflect the reflected beam to the detector. The signal processing system as illustrated in FIG. 3 is used in the embodiment of FIG. 2. The electronics may be shared for signal processing tasks associated with all the beams, or multiple electronic systems may be employed, each system dedicated to a particular beam.

The phase difference between a received frequency modulated laser beam and the reference RF sinusoid generated by local RF oscillator 104 is a function of the optical path length between the laser source and the detector. In any realistic deployment scenario, the distances to the various retro-reflectors are not the same for a system such as FIG. 2. Therefore, the received signals undergo different phase shifts with respect to the phase of the local RF oscillator. Accordingly, the signal processing system in FIG. 3 is expected to be of importance to systems such as FIG. 2.

Embodiments are expected to be of utility in detecting a number of different gases, such as, for example, Carbon Dioxide, Methane, Hydrogen Sulfide, and for detecting Carbon, Deuterium, and Sulfur isotopes of these various gases. Embodiments are expected to provide a phase insensitive FM method for measuring concentration profiles of gas leaks and leak speed over a relatively large monitoring area.

Various modifications may be made to the disclosed embodiments without departing from the scope of the invention as claimed below. Furthermore, it is to be understood in these letters patent that the meaning of "A is coupled to B" is that either A and B are directly connected to each other, or that, although A and B may not be directly connected to each other, there is nevertheless a device or circuit that is connected to both A and B. This device or circuit may include active or passive circuit elements, where the passive circuit elements may be distributed or lumped-parameter in nature. For example, A may be connected to a circuit element that in turn is connected to B, in which case A may be said to be coupled to B.

What is claimed is:

1. An apparatus comprising:
   a frequency modulated laser source;
   a photo-detector to receive radiation from the frequency modulated laser source;
   a band-pass filter coupled to the photo-detector;
   a rectifier coupled to the band-pass filter to provide an output signal;
   a filter to low-pass filter the output signal of the rectifier; and
   a radio frequency oscillator to frequency modulate the frequency modulated laser source at a first tone and a second tone.

2. The apparatus as set forth in claim 1, wherein a harmonic of the difference between the first and second tones substantially matches the center frequency of the band-pass filter.

3. The apparatus as set forth in claim 1, wherein the band-pass filter has a Q factor larger than 2000.

4. The apparatus as set forth in claim 1, wherein the band-pass filter includes a crystal filter.

5. The apparatus as set forth in claim 1, further comprising:
   at least one switch to direct radiation from the frequency modulated laser source in at least two directions.

6. An apparatus comprising:
   a frequency modulated laser source;
   a photo-detector to receive radiation from the frequency modulated laser source;
   a band-pass filter coupled to the photo-detector;
   a rectifier coupled to the band-pass filter to provide an output signal;
   a filter to low-pass filter the output signal of the rectifier; and
   a radio frequency oscillator to frequency modulate the frequency modulated laser source at a single tone.

7. The apparatus as set forth in claim 6, the band-pass filter having a center frequency, wherein the frequency modulated laser source is modulated so that a harmonic of the single tone substantially matches the center frequency of the band-pass filter.

8. The apparatus as set forth in claim 6, wherein the band-pass filter has a Q factor larger than 2000.

9. The apparatus as set forth in claim 8, the band-pass filter having a center frequency, wherein the frequency modulated laser source is modulated so that a harmonic of the single tone substantially matches the center frequency of the band-pass filter.

10. The apparatus as set forth in claim 6, wherein the band-pass filter includes a crystal filter.

11. The apparatus as set forth in claim 10, the band-pass filter having a center frequency, wherein the frequency modulated laser source is modulated so that a harmonic of the single tone substantially matches the center frequency of the band-pass filter.

* * * * *